United States Patent [19]
Gradinger et al.

[11] Patent Number: 5,433,750
[45] Date of Patent: Jul. 18, 1995

[54] BONE REPLACEMENT WITH DIFFERENT REGIONS OF POROSITIES

[75] Inventors: Rainer Gradinger, Munich; Hans Grundei, Luebeck, both of Germany

[73] Assignee: ESKA Medical GmbH & Co., Luebeck, Germany

[21] Appl. No.: 31,151

[22] Filed: Mar. 12, 1993

[30] Foreign Application Priority Data

Mar. 14, 1992 [DE] Germany .................. 42 08 247.1

[51] Int. Cl.⁶ ............................................. A61F 2/28
[52] U.S. Cl. .................................... 623/16; 623/66; 623/23
[58] Field of Search .............. 623/16, 18, 23, 22

[56] References Cited

U.S. PATENT DOCUMENTS

| | | | |
|---|---|---|---|
| 3,808,606 | 5/1974 | Tronzo | 3/1 |
| 3,840,904 | 10/1974 | Tronzo et al. | 623/22 |
| 4,542,539 | 9/1985 | Rowe et al. | 623/16 |
| 4,553,272 | 11/1985 | Mears | 623/1 |
| 4,865,608 | 9/1989 | Brooker, Jr. | 623/23 |
| 4,911,720 | 3/1990 | Collier | 623/16 |

FOREIGN PATENT DOCUMENTS

| | | |
|---|---|---|
| 0159036 | 10/1985 | European Pat. Off. . |
| 0337757 | 10/1989 | European Pat. Off. . |
| 8607873 | 7/1987 | Germany . |
| 3918967 | 12/1989 | Germany . |
| 3917033 | 8/1990 | Germany . |
| 4106971 | 3/1992 | Germany . |

*Primary Examiner*—David Isabella
*Attorney, Agent, or Firm*—Panitch Schwarze Jacobs & Nadel

[57] ABSTRACT

An implant is provided for replacement of bones, especially a joint replacement with an open-mesh three-dimensional structure at least partly covering its surface. The surface structure (1) is in its surface extension divided into at least two discrete zones (A, B, C) with different mesh sizes. After the implantation, bone material grows into the three-dimensional structure. The distribution of the zones of different mesh sizes on the surface of the implant depends on the pore size of the natural spongiosa of the bone onto or into which the implant is to be inserted.

10 Claims, 3 Drawing Sheets

BONE REPLACEMENT WITH DIFFERENT REGIONS OF POROSITIES

FIELD OF THE INVENTION

The invention concerns an implant for replacement of bones, especially a joint replacement with an open-mesh three-dimensional structure at least partly covering its surface.

BACKGROUND OF THE INVENTION

Implants of this type have been in clinical use for approximately 10 years. In contrast to cementable implants, the fixation of the presently stated implants occurs without cement, since the trabecular bones grow into the three-dimensional structure and ossify there. The three-dimensional surface structure of such implants is thoroughly grown through with bone material which, in principle, results in excellent experiences with long-term fixations. Implants of this type are known, for example, from DE-A1-29 10 627, DE-A1-31 06 917 (U.S. Pat. No. 4,718,721) and more recently from DE-U1-90 11 363.

Even when the long-term fixation—as already mentioned—in principle fulfills the desired expectations, the known implants have, nevertheless, the disadvantage that they only form a functional unit with the surrounding bone material in the border areas, in the sense that on account of the different bone thickness structure in areas of the implant, different elastic moduluses in the natural spongiosa of the bone stand in contrast to the uniform surface structure of the implant. In certain areas of the bone spongiosa of a tubular bone, the spongiosa has a rather large cell and pore structure towards the joint ends, but there are areas where the cell and pore size of the bone spongiosa is approximately one to three times smaller than in the first-mentioned area. As an example of such a tubular bone, the human femur can be cited.

It is clear that the trabecular bones, as an integral part of the natural spongiosa, cannot grow well into a homogenous cell and pore structure in the uniform surface structure of the implant. Ultimately, this leads to a prolongation of the healing phase and the reconstruction phase of the bony layers into the implant, and to a shortening of the long-term fixation, because of the fact that the so-called relatives of a trabecular bone group grow into the surface structure, which are not of the group to be attached to a certain location of the spongiosa with a predominating cell and pore structure.

In view of this background, it is the object of the present invention to create an implant with an open-mesh three-dimensional structure at least partly covering its surface, whose healing ability, as well as whose long-term fixation properties, are a clear improvement over the known implants.

SUMMARY OF THE INVENTION

This object is achieved by the implant of the present invention, and other advantageous forms result from the preferred embodiments. Accordingly, it is proposed that the surface structure of the implant in its surface extension is divided into at least two discrete zones of different mesh sizes. By this expression "surface extension" is meant a surface section of the implant, in contrast to the spatial extension, which refers to the thickness or strength of the structure.

The mesh sizes of the zones are preferably adapted to the cell and pore structure of the bone material, which is in contact with the surface structure of the implant after the implantation, in the sense that the respective mesh sizes of the zones correspond approximately in size to the cells and pores of the natural spongiosa, which should grow into and onto the surface structure of the implant. For the spongiosa with a small cell and pore size, there will accordingly be provided a correspondingly smaller mesh size structure on the implant. Similarly, for a spongiosa with a large cell and pore size, there will be provided a zone on the implant with a correspondingly large mesh size.

The cell and pore sizes of the natural spongiosa in tubular bones of man can be catalogued, so that by using this catalog the implants can be produced with corresponding zones of different mesh sizes, depending on which bone part the implant is intended for.

The construction of the implant according to the invention has the result that trabecular bones of the spongy bone, with a given cell and pore size, can grow into the surface structure with a corresponding mesh size. The trabecular bones meet under quasi-natural circumstances, so that a significantly improved growth relationship of the implant can be observed. Furthermore, the implant of the invention improves the properties relating to a long-term fixation, since the "correct" trabecular bones can grow into the "correct" mesh size of the structure, and therefore, the elastic modulus in the natural spongiosa can remain mostly intact despite the presence of the implant.

The largest mesh diameter of a zone of the surface structure is 6 mm; the smallest mesh diameter is 1.5 mm. All the areas between these two end values can be provided for, depending on the natural construction of the spongiosa of the bone, onto or into which the implant is to be placed.

According to a preferred form, at least three zones of the surface structure are provided whose mesh sizes decrease stepwise (zone to zone) from the largest. A specific implant, which is constructed in such a way, is a hip joint shaft. Corresponding to the natural spongiosa in the femur bone, a large mesh diameter of up to 6 mm is present in the proximal region of the implant, whereupon follows a middle zone of a mesh diameter of 2–4 mm, whereupon follows a distal zone, whose mesh diameter can reach down to 1.5 mm.

According to an advantageous further embodiment of the implant, the transition areas from one zone to the neighboring zone of the surface structure have mesh sizes of both bordering zones; that is, both mesh sizes are represented in the spatial depth of the surface structure. This will only be the case in a relatively small transition area. With this construction there will still be discrete zones of the structure with different mesh sizes, but the transitions will be quasi-uniform in the sense of there being a quasi-constant (gradual) transition from one zone to the other. This largely corresponds to the gradual change of the natural spongy materials from one cell and pore size to another cell and pore size.

BRIEF DESCRIPTION OF THE DRAWINGS

The foregoing summary of the invention, as well as the following detailed description of the preferred embodiments, will be better understood when read in conjunction with the appended drawings. For the purpose of illustrating the invention, there are shown in the drawings embodiments which are presently preferred, it

DETAILED DESCRIPTION OF PREFERRED EMBODIMENTS

Figure 1:
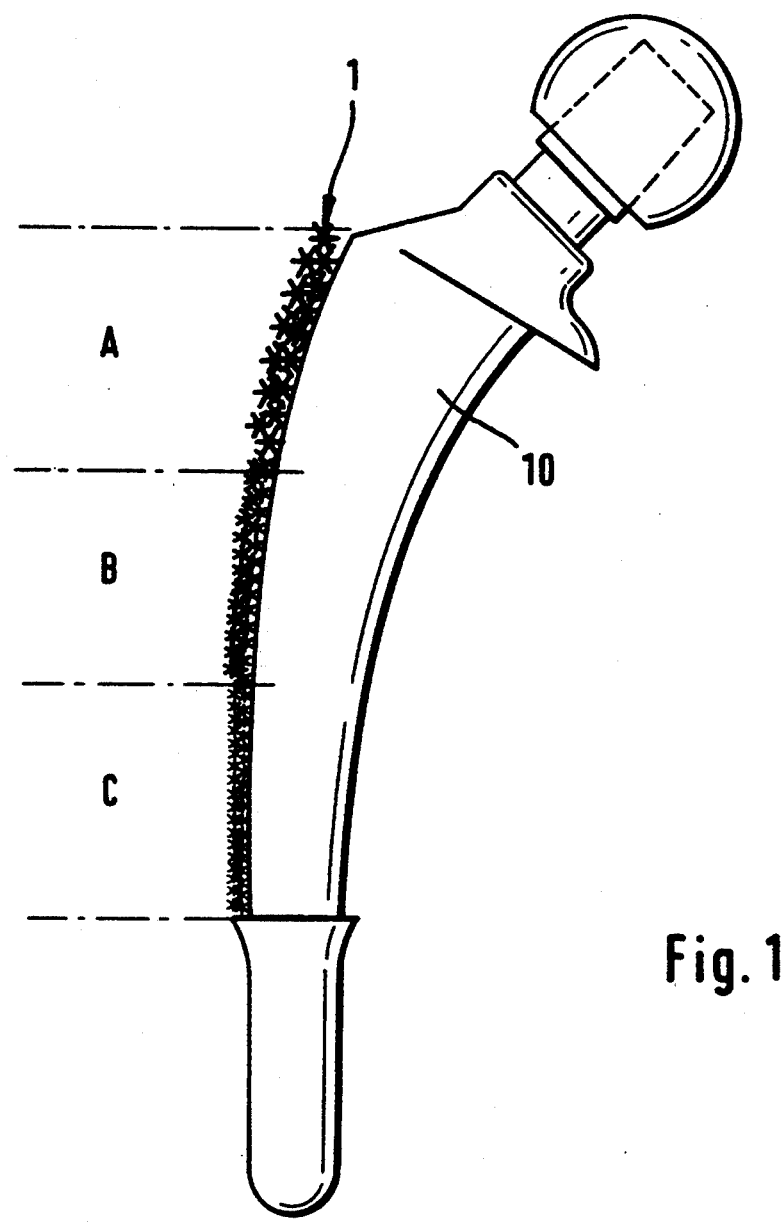
FIG. 1 is an implant for a hip joint shaft with an open-mesh three-dimensional structure at least partly covering its surface.

In the embodiment of the inventive implant according to FIG. 1 there is shown a conventional hip joint shaft 10. The massive core of the shaft 10 is provided with, as schematically displayed, an open-mesh three-dimensional structure 1 at least partly covering its surface. Bone material grows into this surface structure after the implantation, and thereby, causes permanent fixation of the implant in the bone.

According to the invention, the surface structure 1 of the hip joint shaft 10 is divided into three discrete zones A, B and C. The largest mesh size of the surface structure is shown in zone A; in zone B a medium mesh size; and finally in zone C the smallest mesh size. In the displayed embodiment the mesh sizes are formed from particles which are described in DE-C1-41 06 971 (U.S. Pat. No. 5,178,201). A different material for production of the surface structures can also be used, for example, prepared filter sponges, as described in DE-C1-39 17 033 and in DE-C2-39 28 394 (U.S. Pat. Nos. 5,042,560 and 5,016,702, respectively).

The selection of mesh sizes of the surface structure 1 in the zones A, B and C depends on the natural cell and pore widths (diameters) of the spongiosa in the femur bone. The mesh sizes of the surface structure 1 are adapted to the cell and pore sizes of the spongiosa; that is, in the proximal region of the hip joint end relatively large, in the distal region relatively small.

Figure 2:
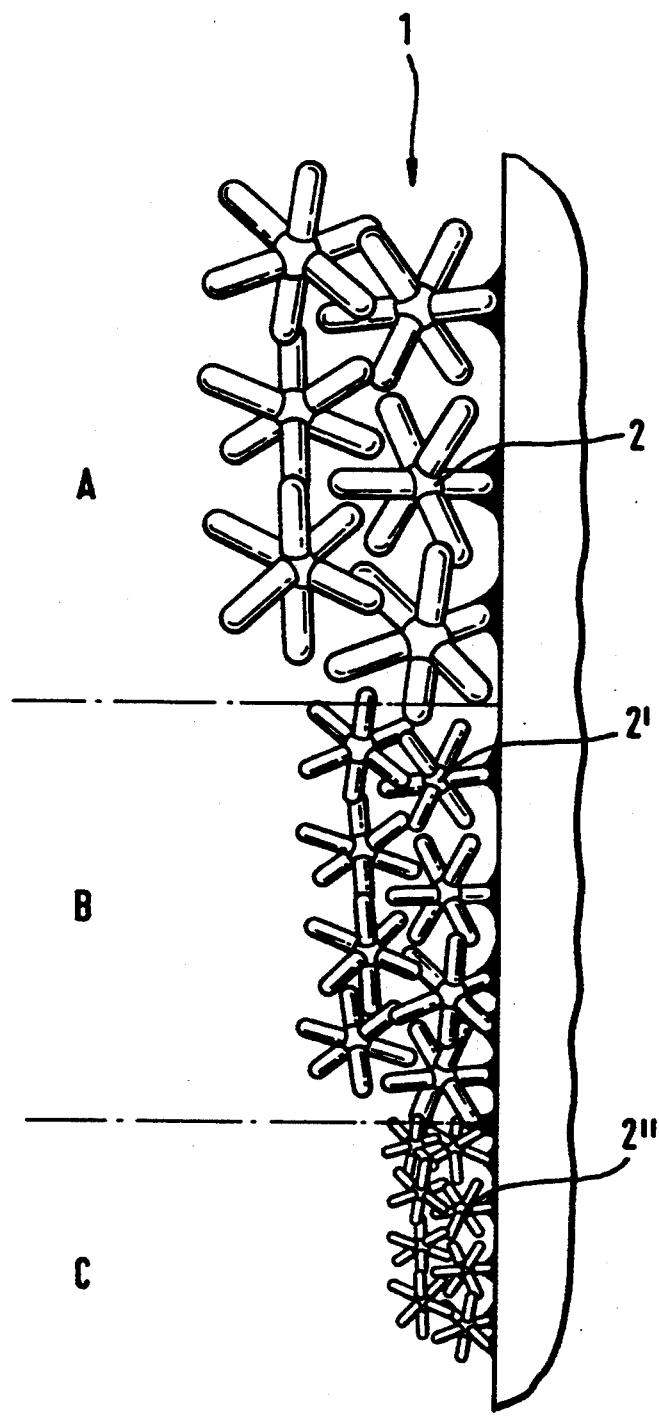
FIG. 2 is a schematic view of several zones of the surface structure of an implant according to the invention.
Figure 3:
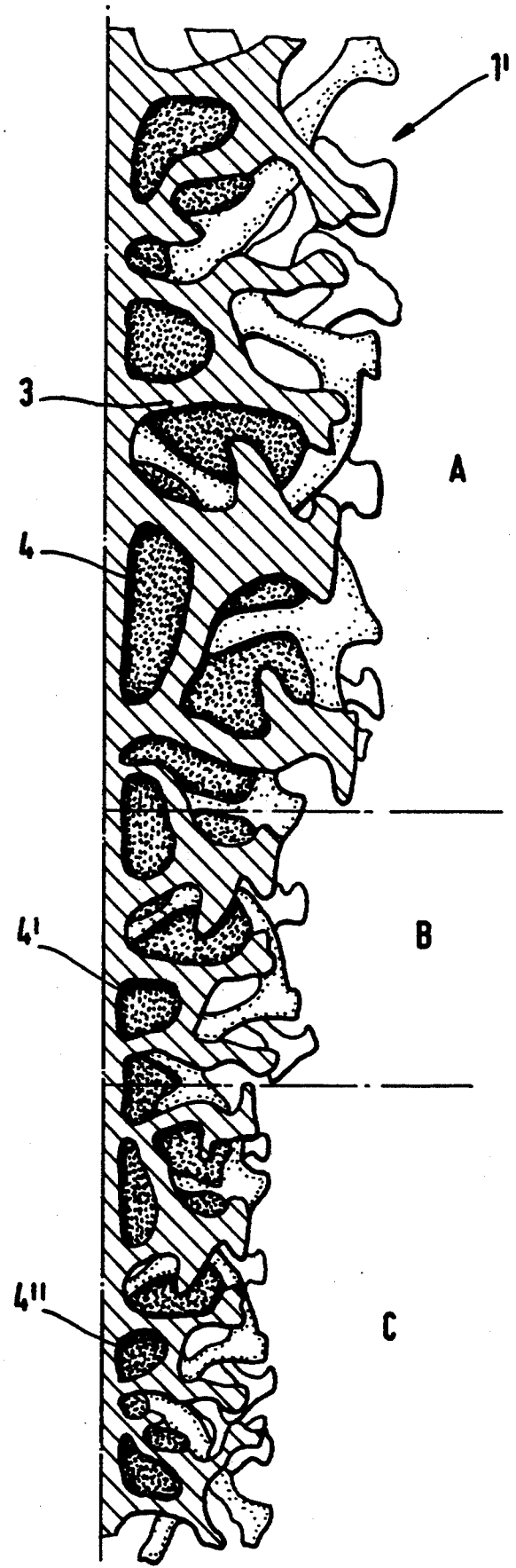
FIG. 3 is a similar view as FIG. 2, but with a differently constructed surface structure.

FIG. 2 shows schematically an enlarged view of the surface structure 1 of the implant according to the invention. Clearly recognizable are the discrete zones A, B and C with the different mesh sizes of the surface structure 1. These are achieved through the particles 2, 2' and 2" of different size. As already mentioned above, these different mesh sizes can also be substituted instead with different sized particles, also with reticulated filter sponges with different mesh sizes, as starting material in the production procedure. A surface structure 1' of an implant, made with reticulated filter sponges as starting material of a lost positive process (DE-C2-39 28 394 or U.S. Pat. No. 5,016,702), is shown in FIG. 3. Here also the discrete zones A, B and C are clearly distinguishable, the different sized meshes 4, 4' and 4" bordered by the struts 3 being shown.

It is not absolutely necessary that the surface structures 1 and 1' decrease in their strength as the size of the particles decreases in the discrete zones A, B and C. It is essential that the trabecular bones of the relevant spongiosa regions of the bone, against which the zones A, B and C will lie, have mesh sizes in the surface structure 1 into which they can grow, and which correspond approximately in their mesh size to the cell and pore size which would develop in the respective trabecular bones of the natural spongiosa.

The present invention may be embodied in other specific forms without departing from the spirit or essential attributes thereof and, accordingly, reference should be made to the appended claims, rather than to the foregoing specification as indicating the scope of the invention.

We claim:

1. An implant for the replacement of bones, said implant having a bone contacting surface, said bone contacting surface being at least partially covered by an open-mesh three-dimensional structure (1,1'), wherein said structure has at least two discrete zones (A, B, C), said zones extending sequentially adjacent to each other along the bone contacting surface, and wherein said structure has predetermined mesh opening sizes which differ from zone to zone for receiving ingrowth of different size cells and pores of the bone spongiosa.

2. The implant according to claim 1, wherein the mesh openings differ in diameter in a range of from 1.5 mm to 6 mm.

3. The implant according to claim 1, wherein the structure has at least three of said zones, and the mesh opening size of the structure decreases stepwise from zone to zone.

4. The implant according to claim 2, wherein the structure has at least three of said zones, and the mesh opening size of the structure decreases stepwise from zone to zone.

5. The implant according to claim 1, wherein the structure has at least three of said zones, and the mesh opening size of the structure in a zone proximal to a joint between bones is larger than the mesh opening size of the structure in a zone distal from the joint.

6. The implant according to claim 2, wherein the structure has at least three of said zones, and the mesh opening size of the structure in a zone proximal to a joint between bones is larger than the mesh opening size of the structure in a zone distal from the joint.

7. The implant according to claim 3, wherein the structure has at least three of said zones, and the mesh opening size of the structure in a zone proximal to a joint between bones is larger than the mesh opening size of the structure in a zone distal from the joint.

8. The implant according to claim 1, wherein the structure in a transition area between two adjacent zones (A and B, or B and C) has the mesh opening sizes of both adjacent zones.

9. The implant according to claim 2, wherein the structure in a transition area between two adjacent zones (A and B, or B and C) has the mesh opening sizes of both adjacent zones.

10. The implant according to claim 3, wherein the structure in a transition area between two adjacent zones (A and B, or B and C) has the mesh opening sizes of both adjacent zones.

* * * * *